United States Patent
Wahlström et al.

(10) Patent No.: US 6,998,512 B2
(45) Date of Patent: Feb. 14, 2006

(54) FIBROUS MATERIAL LAYER, METHOD FOR ITS MANUFACTURE, AND ABSORBENT ARTICLE COMPRISING THE MATERIAL LAYER IN QUESTION

(75) Inventors: Johan Wahlström, Göteborg (SE); Lena Björnström, Göteborg (SE); Leif Alm, Göteborg (SE); Fredrik Krook, Göteborg (SE); Sven-Erik Johansson, Bollebygd (SE)

(73) Assignee: SCA Hygiene Products AB, Gothenburg (SE)

( * ) Notice: Subject to any disclaimer, the term of this patent is extended or adjusted under 35 U.S.C. 154(b) by 140 days.

(21) Appl. No.: 10/255,939

(22) Filed: Sep. 27, 2002

(65) Prior Publication Data

US 2003/0073967 A1 Apr. 17, 2003

Related U.S. Application Data

(63) Continuation of application No. PCT/SE01/00646, filed on Mar. 26, 2001.

(30) Foreign Application Priority Data

Mar. 27, 2000 (SE) .......................................... 0001067-8

(51) Int. Cl.
*A61F 13/15* (2006.01)

(52) U.S. Cl. ....................... 604/378; 604/379; 604/384; 604/380

(58) Field of Classification Search ................. 604/382, 604/378, 365, 374, 366, 383, 384; 428/170, 428/171, 122, 167
See application file for complete search history.

(56) References Cited

U.S. PATENT DOCUMENTS

| 4,578,070 A | 3/1986 | Holtman |
| 5,752,945 A | 5/1998 | Mosley et al. |
| 5,843,064 A | 12/1998 | Koczab |
| 6,414,216 B1 | 7/2002 | Malowaniec |

FOREIGN PATENT DOCUMENTS

| DE | 197 32 550 C1 | 3/1999 |
| EP | 0 674 891 A2 | 10/1995 |
| EP | 0 937 792 A1 | 8/1999 |
| GB | 2 209 672 A | 5/1989 |
| WO | 94/08789 | 4/1994 |
| WO | 97/02133 A1 | 1/1997 |
| WO | 99/27879 | 6/1999 |

*Primary Examiner*—John J. Calvert
*Assistant Examiner*—Jacqueline Stephens
(74) *Attorney, Agent, or Firm*—Buchanan Ingersol PC

(57) ABSTRACT

Fibrous material layer intended to be incorporated in an absorbent article. The layer (5) comprises at least two webs of tow fibers arranged on top of each other, which are bonded to each other into a laminate by means of a bonding pattern, and where one is corrugated and the other web is substantially smooth, wherein the corrugated web exhibits a more open structure in comparison to the smooth web. A method of manufacturing the layer (5) in question, in which method at least two separate webs (15a, b) of opened and into a layer spread-out tow are fed into a bonding station (20), which webs exhibit different web tensions and/or web speeds, and that the webs (15a, b) with maintained relative difference in web tension and/or web speed are bonded together in said bonding pattern (10) into a laminate.

10 Claims, 3 Drawing Sheets

FIBROUS MATERIAL LAYER, METHOD FOR ITS MANUFACTURE, AND ABSORBENT ARTICLE COMPRISING THE MATERIAL LAYER IN QUESTION

CROSS-REFERENCE TO RELATED APPLICATIONS

The present application is a continuation of PCT/SE01/00646 filed on Mar. 26, 2001, which was published in English on Oct. 4, 2001, the entire contents of which is hereby incorporated hereby reference.

BACKGROUND OF THE INVENTION

1. Field of the Invention

The present invention relates to a fibrous material layer intended to be incorporated in an absorbent article such as a diaper, a pant diaper, an incontinence guard, a sanitary napkin and the like, of the type comprising a liquid-pervious topsheet, a liquid-impermeable backsheet, and an absorbent body applied therebetween.

2. Background of the Invention

Absorbent articles of the above-mentioned type are intended for absorption of body fluids such as urine and blood. As a liquid-pervious topsheet, they usually use a nonwoven material, e.g., of spunbond type, which during use is facing the user. It is also previously known to arrange an acquisition layer, between the topsheet and the absorbent body, having the ability to rapidly receive large liquid quantities and to distribute the liquid and store it temporarily before it is absorbed into the underlying absorbent body. This is of great importance, particularly in the thin, compressed absorbent bodies of today which often have a high content of so-called superabsorbents, which certainly have a high absorption capacity but in many cases an absorption rate which is too low to be able to instantaneously absorb the large quantity of liquid which may be emitted within a few seconds when urinating.

A porous, relatively thick acquisition layer, e.g. in the form of a fiber wadding, a carded fiber web, or another type of fiber material, has a high instantaneous liquid acquisition and can store the liquid temporarily until it has been absorbed by the absorbent body. Porous foam materials behave in the same way. Subsequently, the liquid successively is drained into the underlying absorbent core, after which the acquisition layer once again has the capacity to receive liquid from another wetting.

Examples of absorbent articles comprising such porous acquisition layers are disclosed in e.g. U.S. Pat. No. 3,371,667, EP-A-0,312,118 and EP-A-0,474,777.

The present materials which are used as acquisition layers in absorbent articles function well most of the time, but are relatively expensive and may sometimes exhibit an insufficient acquisition rate, particularly in the second and third wetting when large liquid quantities are concerned.

Another problem is that conventional liquid-pervious topsheet materials utilized for absorbent articles of this type, usually a nonwoven material of synthetic fibers, e.g., a spunbond material, often exhibit a liquid acquisition rate which is inferior to the one of the acquisition layer, wherein liquid is able to leak out from the article before it reaches the acquisition layer. Naturally, this problem can be solved by means of utilizing a topsheet material which is very open and thereby exhibits a high liquid acquisition rate. Such an open topsheet material, however, can cause problems with a strength which is too low, and with sharp fiber ends from the acquisition layer which penetrate the open topsheet material and irritate the user.

A material layer of the type mentioned in the introduction is known from WO 99/27876, i.e., a layer of continuous fibers, so-called tow, which have been bonded together in dots, lines or spots of a bonding pattern but which otherwise are substantially unbonded to each other. The material layer exhibits a high liquid acquisition rate also in repeated wettings, high strength and wear resistance, and high comfort. However, there is still room for further development of such a material, particularly when the liquid acquisition properties and the surface dryness are concerned.

OBJECTS AND SUMMARY

An object of the present invention is to achieve a fibrous material layer of the above-mentioned type, which material layer exhibits improved liquid acquisition properties and surface dryness. According to one embodiment the invention, this has been achieved by means of a comprising at least two webs of tow fibers arranged on top of each other, which webs are bonded together into a laminate by means of a bonding pattern and where one web is corrugated and the other web is substantially smooth, wherein the corrugated web exhibits a more open structure in comparison to the smooth web.

Furthermore, one embodiment of the invention relates to a method of manufacturing a material layer of the above-mentioned type, in which method at least two separate webs of opened and into a layer spread-out tow are fed into the bonding station, which webs exhibit different web tensions and/or web speeds, and the webs with a maintained relative difference in web tension and/or web speed are bonded together in dots, spots or lines of said bonding pattern into a laminate, wherein the web exhibiting the lower web tension, alternatively the higher web speed, is slowed down and becomes corrugated at the feed end of the bonding station, while the other web remains substantially smooth, and the laminate after the bonding is transported further on from the bonding station with a web tension/web speed which is substantially identical to the lower web tension/lower web speed.

Furthermore, embodiments of the invention relate to an absorbent article such as a diaper, a pant diaper, an incontinence guard, a sanitary napkin, and the like, comprising a material layer of the above-described type.

Additional features of the invention are evident from the following claims and the description.

The material layer can be utilized as a liquid acquisition layer beneath a topsheet material, as a topsheet material, or as an integrated topsheet material/liquid acquisition layer.

BRIEF DESCRIPTION OF THE DRAWINGS

In the following, the invention will be described in greater detail with reference to a few embodiments shown in the attached drawings.

DETAILED DESCRIPTION OF PREFERRED EMBODIMENTS

Figure 1:
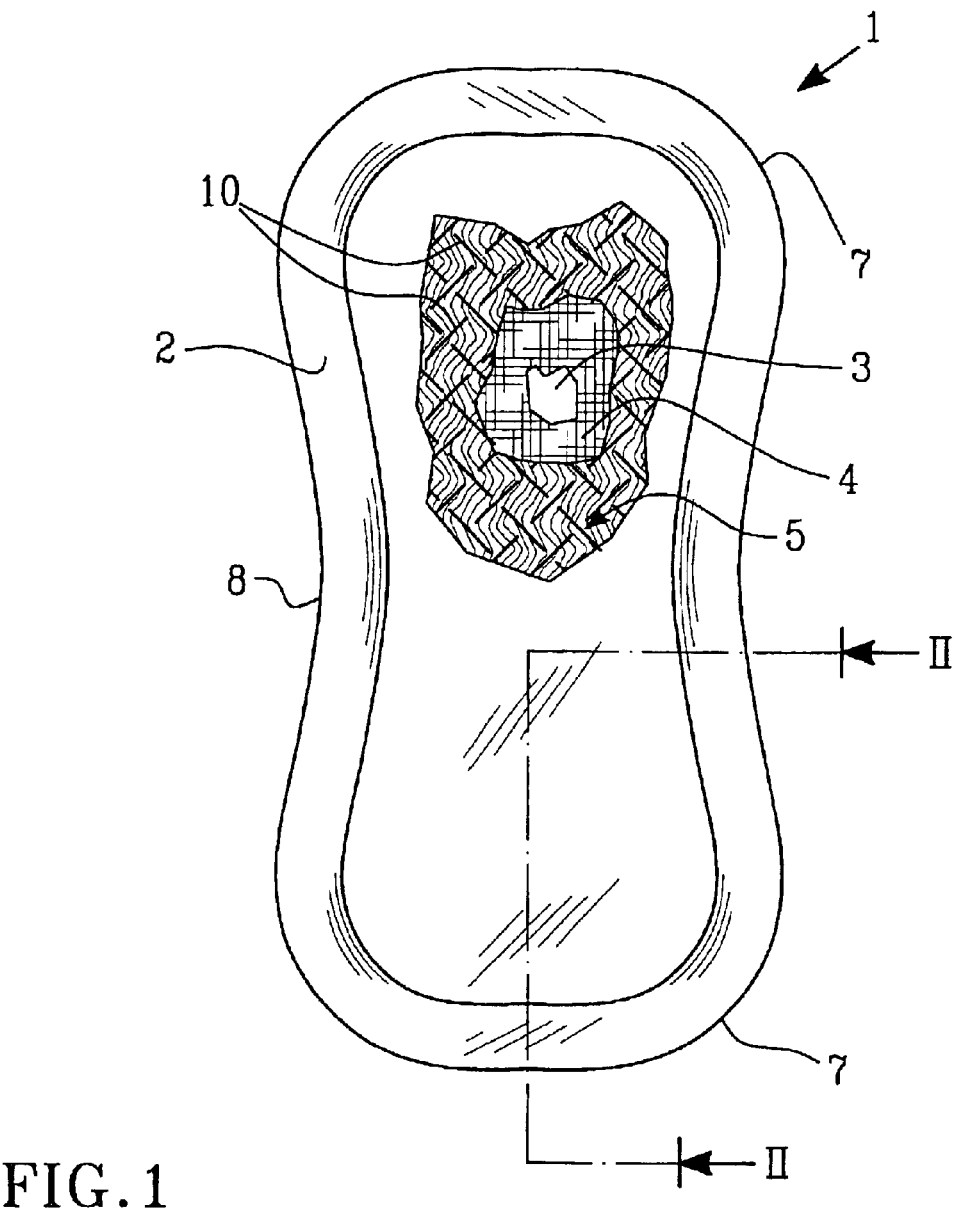
FIG. 1 is a plan view of an absorbent article in the form of an incontinence guard.
Figure 2:
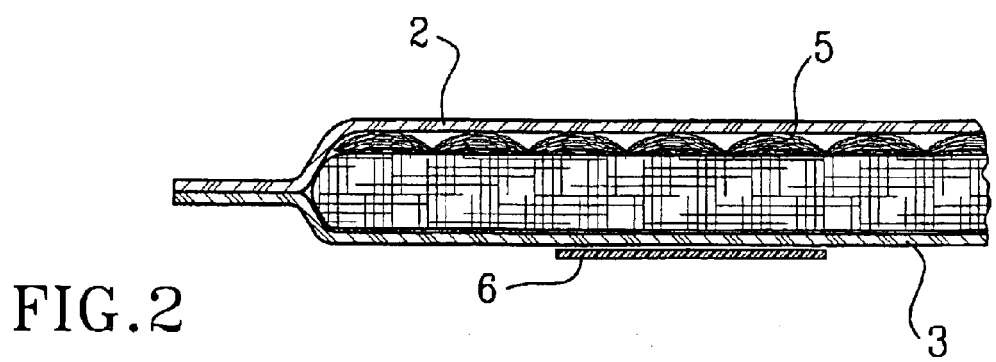
FIG. 2 is a section along the line II—II in FIG. 1.

FIGS. 1 and 2 show an embodiment of an incontinence guard 1, which comprises a liquid-pervious topsheet 2, a liquid-impermeable backsheet 3 and an absorbent body 4 enclosed therebetween. Furthermore, a porous and resilient liquid acquisition layer 5 is arranged between the liquid-pervious topsheet 2 and the absorbent body 4.

The liquid-pervious topsheet 2 can consist of a nonwoven material, for example a spunbond-material of synthetic filaments, a meltblown-material, a thermo-bonded material or a bonded carded fiber material. The liquid-impermeable backsheet 3 can consist of a plastic film, a nonwoven material which has been coated with a liquid-arresting material or a hydrophobic nonwoven material which resists liquid penetration.

The topsheet 2 and the backsheet 3 have a somewhat larger extension in the plane than the absorbent body 4 and the liquid acquisition layer 5 and extend outside the edges of these. The layers 2 and 3 are mutually connected within the projecting portions, for example by means of gluing or welding by means of heat or ultrasonics.

The absorbent body 4 can be of any conventional type. Examples of commonly occurring absorption materials are cellulosic fluff pulp, tissue layers, highly absorbent polymers (so-called superabsorbents), absorbent foam materials, absorbent nonwoven materials and the like. It is common to combine cellulosic fluff pulp with superabsorbents in an absorbent body. It is also common with absorbent bodies constituted of layers of different materials having different properties when liquid acquisition capacity, distribution ability, and storage capacity are concerned. This is well-known to the person skilled in the art, and will therefore not be described in any greater detail. The thin absorbent cores which are common in, for example, baby diapers and incontinence guards often consist of a compressed mixed or layered structure of cellulosic fluff pulp and superabsorbent.

On the outside of the liquid-impermeable backsheet 3, fastening means in the form of longitudinal strings 6 of self-adhesive glue are arranged. An incontinence guard of the type shown in FIG. 1 primarily is intended to be used by persons with relatively mild incontinence problems, and is easily accommodated inside a pair of regular underpants. Thereby, the fastening means 6 serve to keep the incontinence guard in its place inside the underpants during the use. Naturally, a number of other glue patterns, e.g. transverse patterns, are conceivable, as well as other types of fastening means, such as velcro surfaces, push buttons, girdles, special underpants, or the like.

The incontinence guard 1 is preferably hourglass-shaped with wider end portions 7, and a narrower crotch portion 8 located between the end portions. The crotch portion 8 is the portion of the incontinence guard which during use is intended to be applied in the crotch of the user to serve as a receiving surface for the excreted body fluid.

It should be noted that the incontinence guard and diaper shown in the drawings and described above only constitute a pair of non-limiting embodiments of an absorbent article. Accordingly, the shape and other design of the article can be varied. The absorbent article also can be constituted of a pant diaper, a sanitary napkin or the like. The absorbent article can be either of a disposable or multiple-use type. However, when products of multiple-use type are concerned, other materials than the above-described are relevant as a liquid-pervious topsheet and as an absorbent body.

A porous and resilient acquisition layer 5, having the ability to rapidly receive large liquid quantities and to distribute the liquid and store it temporarily before it is absorbed by the underlying absorbent body 4, is arranged between the liquid-pervious topsheet 2 and the absorbent body 4. This property should essentially be maintained also after wetting of the material. The acquisition layer 5 may either cover the entire absorbent body 4, extend outside of it, or only cover the central portions of the absorbent body.

According to the invention, the acquisition layer 5 is constituted of a layer of continuous fibers 9, so-called tow, which have been bonded together in dots, lines or spots of a bonding pattern 10 but which otherwise are substantially unbonded to each other. In the embodiment shown in FIG. 1, the bonding pattern 10 is constituted of a line pattern with short lines arranged in a zigzag configuration. The bonding pattern is accomplished, e.g., by means of welding with ultrasonics or other thermo-bonding. Examples of other suitable thermo-bonding methods are pattern calendering, laser bonding, etc. A prerequisite for this is that at least part of the fibers included in the tow are thermoplastic. Examples of thermo-fibers are polyolefines, polyamides, polylactide, polyester, and the like. Also so-called bicomponent fibers are included. As an alternative to thermo-bonding, bonding may be accomplished with a binding agent by means of so-called print-bonding or dot-bonding, or in a mechanical way with so-called entanglement by means of needling or water jets. Primarily, the choice of bonding type is determined by the type of fibers utilized in the tow.

Naturally, the design of the bonding pattern 10 can be varied within wide limits. The pattern can be in the form of dots, spots, or preferably lines. The lines can be straight and/or curved and the length can vary from a few millimeters to a transverse or oblique extension across the entire product. Preferably, the lines extend across or obliquely across the length direction of the fibers 9, so that a plurality of fibers are bonded to each other by each bonding line. It is also advantageous that different bonding lines overlap each other, as seen in the transverse direction of the article, so that a main proportion of the fibers are bonded at least along some portion of their length.

The bonding pattern can be identical across the entire acquisition layer 5, or be different in different portions of it. Accordingly, the bonding pattern for example may be more sparse within the wetting region and more dense outside of it. It is also possible to design the bonding pattern in such a way that the layer 5 obtains different heights in different portions of the product, for example a smaller height in the central portions and a larger height in the surrounding edge portions, in order to create a bowl-shape which provides a liquid receiving volume, alternatively a larger height in the central portions than in the surrounding edge portions in order to create an improved body contact.

Figure 3:
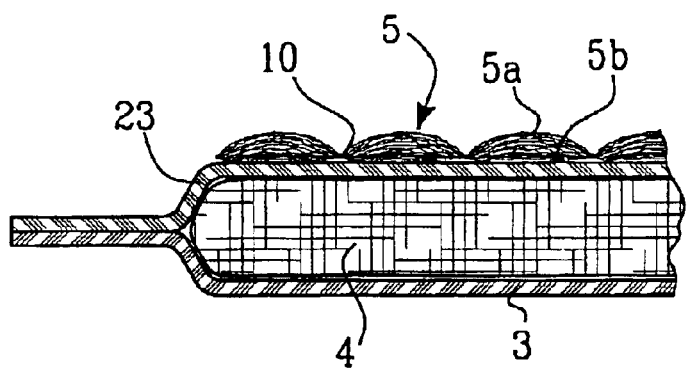
FIG. 3 is a corresponding section through a modified embodiment.

FIG. 3 shows a modified embodiment, in which the layer 5 of continuous filaments 9 has been utilized as a combined liquid-pervious topsheet material and acquisition layer, i.e. which is to be located directly against the skin of the user. In this case, the layer 5 is supported by a carrier material 23, for example, in the form of a nonwoven material.

According to another embodiment, which is not shown, the acquisition layer 5 is covered by a topsheet material 2, through which an aperture has been made at the intended wetting region, wherein the acquisition layer 5 in this region is exposed directly towards the user. Several smaller apertures can be provided instead of a single, larger aperture.

Figure 4:
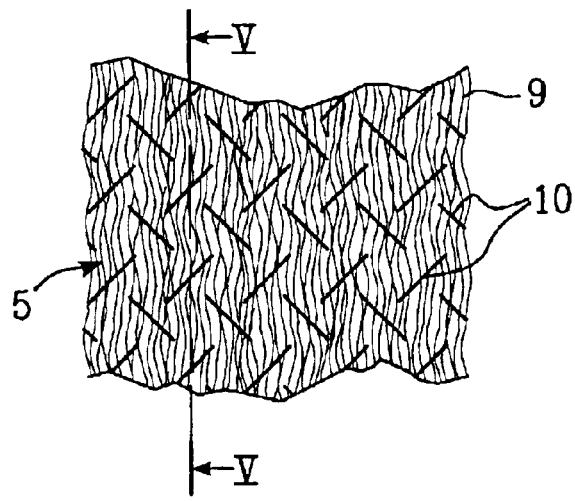
FIG. 4 shows a portion of a fibrous material layer according to an embodiment of the invention, in a schematic way.
Figure 5:
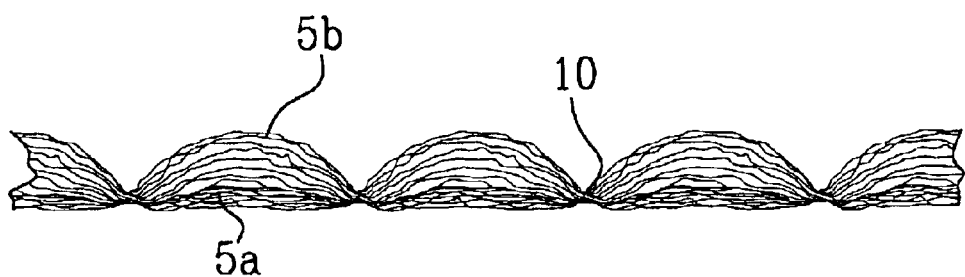
FIG. 5 shows, in magnification, a schematic section along the line V—V in FIG. 4.

FIGS. 4 and 5 are schematic representations of a portion of a layer 11 of continuous fibers 9 which have been bonded in a simple bonding pattern 10 with short lines arranged in a zigzag configuration. Except at the bonding sites, the fibers 9 are unbonded to each other.

Figure 6:
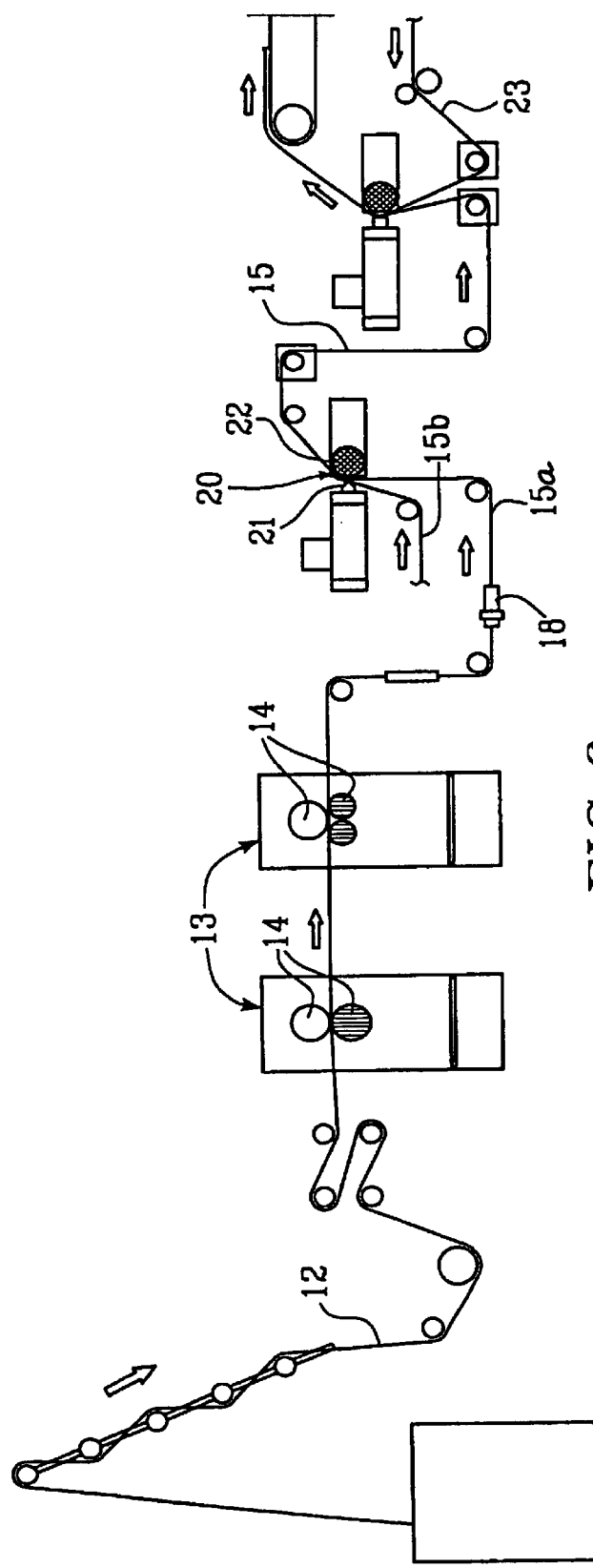
FIG. 6 is a schematic side view of a process device for carrying out the method according to the invention.

The method of manufacturing the material layer according to the invention comprises several steps, which is evident from FIG. 6 in a schematic way. Fiber tow 12 is delivered in bags, or in the form of bales or rolls of continuous fibers, which either are straight, crimped or curled. Crimped or curled fibers are preferred in this case, since they give a very open and airy structure. The fibers in the tow may be of an optional, suitable material such as polyethylene, polypropylene, polyamide, polyester, polylactide, polyvinyl acetate, cellulose acetate, regenerated cellulose fibers such as viscose and rayon, or of a bi-component type with a sheath of a polymer having a lower melting point and a core of polymer having a higher melting point. Particularly preferred are such fibers which exhibit high resiliency, for example polyester, co-polyester or polypropylene.

The fiber coarseness may vary, but is suitably within the interval 0.5–50 dtex, preferably 1.5–25, and most preferably 2–15 dtex, when the material is to be used as an acquisition material or as a combined topsheet material/acquisition material. The open, airy structure in combination with the relatively coarse fiber dimension provides a very rapid liquid acquisition. Furthermore, the material is strong owing to the longitudinal continuous fibers which provide strength in the longitudinal direction, and the bonding pattern which provides strength in the transverse direction.

In this case, the grammage of the bonded fiber tow should be within the interval 10–200 g/m$^2$, preferably 30–150, and most preferably 30–100 g/m$^2$.

The bales or the like are opened in special opening devices, wherein the fibers are separated from each other, stretched out and spread out into an essentially uniformly thick layer. The layer is bonded in a desired bonding pattern as described above, and is cut into suitable lengths either before or after application in an absorbent article. Alternatively, the bonding may take place after the cutting. Tow is a relatively cheap delivery form of fibers in comparison to nonwoven, waddings, and the like which normally are used as acquisition materials.

As is evident from FIG. 6, the opening device 13 comprises one or several threaded roll pairs 14, each consisting of a threaded roll and a counter roll between which the fiber tow 12 is fed in and which accomplish a separation of the individual fibers. During their passage between the threaded rolls 14, the fibers are stretched out. Such types of opening devices are of a conventional type, and are commercially available in different designs.

According to the embodiment shown in FIG. 6, the opened fiber tow, now consisting of a spread-out layer of separated, individual fibers 9 is led through an ejector 18 which blows air into the material web 15a substantially in the longitudinal direction thereof. This through-air blowing is important in order to obtain the desired volume and bulkiness of the material web. The material is fed through the ejector 18 which in an enclosed chamber blows air across and along the feeding direction of the material. In this way, an improved mixing of the fibers is obtained which results in each fiber becoming less dependent on the adjacent fibers. In addition, the fluffiness of the material web is markedly increased, particularly in case the fibers are crimped or helically curled.

In addition to the steps which are represented in a schematic way in FIG. 6, the process also may include features disclosed in EP-A-0 937 792, the contents of which is hereby included by reference.

Thereafter, the material web 15a is fed into a bonding station 20, which in the shown embodiment is constituted of an ultrasonic welding device. This comprises an ultrasonic horn 21 arranged opposite a patterning roll 22.

A second material web 15b, which like the first material web 15a consists of opened tow which has been spread out into a layer, is fed into the bonding station 20 simultaneously in order to be laminated to the first material web 15a therein. On its way from the opening device to the bonding station, the second material web 15b suitably has been subjected to a similar treatment as the first material web 15a. The two webs 15a and 15b are fed into the bonding station 20 with different web tensions and/or web speeds.

In the bonding station 20, while maintaining the relative difference in web tension and/or web speed, the two material webs 15a and 15b are bonded together in dots, spots or lines of a bonding pattern into a laminate. Thereby, the web 15b exhibiting the lower web tension, alternatively the higher web speed, is slowed down and becomes corrugated at the feed end of the bonding station, while the other web 15a remains substantially smooth. After the bonding, the laminate 15 is fed further on from the bonding station 20 with a web tension/web speed which is substantially equal to the lower web tension/lower web speed.

The corrugated material web 15b will form "ridges" 5b (FIG. 5) between the bonding sites 10, in which "ridges" the structure is more open, i.e., the capillaries are larger, than in the portion of the material web 15a which remains smooth and which is denoted with 5a in FIG. 5. In this way, a capillary gradient will be created in the layer 5, which gradient will promote the liquid transport through, and improve the surface dryness of, the layer 5.

Possibly, the material webs 15a and 15b can exhibit different grammages. For example, the material web which remains smooth can exhibit a lower grammage than the corrugated one. Furthermore, the material webs can contain different types of fibers when coarseness, polymer composition, surface finish, crimp, etc. are concerned, in order to obtain the desired properties when liquid acquisition, surface dryness, weldability, etc., are concerned. It is also possible to join more than two material webs into a laminate by means of the described method with a difference in web tension and/or feeding speed.

As mentioned above, also other thermo-bonding methods such as pattern calendering, laser bonding, etc., can be utilized. As an alternative to thermo-bonding, bonding may be accomplished with a binding agent by means of so-called print-bonding or dot-bonding, or in a mechanical way with entanglement by means of needling or water jets.

Possibly, after the pattern-bonding, the material web 15 can be laminated together with a nonwoven material 23 by means of thermo-bonding, e.g., ultrasonic welding, or gluing. This is done against the smooth material web 15a. The nonwoven material 23 can be laminated to the material web 15 either across the entire width of this, or in the form of strips which only are laminated to the edges of the material web. The nonwoven material 15, which can be hydrophobic or hydrophilic, partly has the task to prevent liquid from spreading outwards toward the edges of the absorbent product, and partly to prevent rewetting of liquid towards the skin of the user.

After this, the pattern-bonded material web 15, which possibly has been laminated to a nonwoven material, either can be winded onto a storage roll, or be fed directly into a diaper machine or the like, where it is applied as a layer in an absorbent article such as a diaper, pant diaper, incontinence guard, sanitary napkin, or the like.

Although only preferred embodiments are specifically illustrated and described herein, it will be appreciated that many modifications and variations of the present invention are possible in light of the above teachings and within the purview of the appended claims without departing from the spirit and intended scope of the invention.

What is claimed is:

1. A fibrous material layer adapted to be incorporated in an absorbent article comprising a liquid-pervious topsheet, a liquid-impermeable backsheet, and an absorbent body applied therebetween, wherein the article comprises a layer of continuous tow fibers, which have been bonded together in dots, lines or spots of a bonding pattern, but which otherwise are substantially unbonded to each other, the layer comprises:

at least two webs of tow fibers arranged on top of each other, which webs are bonded to each other in a laminate by means of said bonding pattern, and where one web is corrugated and the other web is substantially smooth, wherein the corrugated web exhibits a more open structure in comparison to the substantially smooth web.

2. The fibrous material layer according to claim 1, wherein tow fibers of different coarseness are utilized in the different webs.

3. The fibrous material layer according to claim 1 wherein that tow fibers having different properties are utilized in the different webs.

4. The fibrous material layer according to claim 3, wherein the different properties may be at least one of hydrophilicity/hydrophobicity, modulus of elasticity and crimp, etc., are utilized in the different webs.

5. The fibrous material layer according to claim 1, wherein the different webs exhibit different grammages.

6. A method for manufacturing a fibrous material layer adapted to be incorporated in an absorbent article, starting from at least one bundle of continuous tow fibers, which is opened and where the fibers are separated and spread out into a layer having a desired fiber distribution, after which the layer in a bonding station is bonded together in dots, spots or lines of a bonding pattern but where the fibers otherwise are substantially unbonded to each other, the method comprising:

feeding at least two separate webs of opened and spread-out tow into the bonding station, which webs exhibit different web tensions or web speeds, bonding together the webs with maintained relative difference in web tension or web speed in dots, spots or lines of said bonding pattern into a laminate, wherein the web exhibiting the lower web tension or the higher web speed becomes corrugated at the feed end of the bonding station while the other web remains substantially smooth, and feeding the laminate after the bonding on from the bonding station with a web tension/web speed which is substantially equal to the lower web tension/lower web speed.

7. A method according to claim 6, wherein said fibrous material layer, against its smooth material web, is laminated to a nonwoven material across at least a portion of its width.

8. An absorbent article, comprising:

a liquid-pervious topsheet, a liquid-impermeable backsheet, an absorbent body applied therebetween, a fibrous material layer having at least two webs of tow fibers, the at least two webs bonded to each other in a bonding pattern of dots, lines, or spots, but which are otherwise substantially unbonded to each other, and where one web is corrugated and the other web is substantially smooth, and the corrugated web exhibits a more open structure in comparison to the substantially smooth web.

9. An absorbent article according to claim 8, wherein the material layer is utilized as a combined liquid-pervious topsheet and liquid acquisition layer.

10. An absorbent article according to claim 8, wherein the material layer is utilized as a liquid acquisition layer applied between the liquid-pervious topsheet and the absorbent body.

* * * * *